United States Patent [19]

Cohen et al.

[11] Patent Number: 5,593,303
[45] Date of Patent: Jan. 14, 1997

[54] ATTACHMENT OF ORTHODONTIC BRACKETS

[76] Inventors: Morton Cohen, 647 Meadowbrook Dr., Huntingdon Valley, Pa. 19006; Elliott Silverman, 1 Spring La., Linwood, N.J. 08221

[21] Appl. No.: 327,233

[22] Filed: Oct. 21, 1994

Related U.S. Application Data

[63] Continuation-in-part of Ser. No. 215,266, Mar. 21, 1994, abandoned.

[51] Int. Cl.$^6$ .................................................. A61C 3/00
[52] U.S. Cl. ........................................................... 433/9
[58] Field of Search .......................... 433/8, 9; 523/116

[56] References Cited

U.S. PATENT DOCUMENTS

| | | | |
|---|---|---|---|
| 3,895,445 | 7/1975 | Silverman et al. | 32/14 R |
| 4,342,677 | 8/1982 | Muramatsu et al. | 523/116 |
| 4,775,592 | 10/1988 | Akahere et al. | 433/228.1 X |
| 4,808,228 | 2/1989 | Randklev | 433/228.1 X |
| 4,820,545 | 4/1989 | Negrych | 433/228.1 X |
| 4,936,775 | 6/1990 | Bennett | 433/220 |
| 5,063,257 | 11/1991 | Akahane et al. | 523/116 |
| 5,151,453 | 9/1992 | Ibsen et al. | 522/14 |

OTHER PUBLICATIONS

"Glass Ionomer Cements Used in Bonding Materials for Metal Orthodontic Brackets. An in vitro Study", Oen, J. O. et al., *European Journal of Orthodontics*, 13, 187–191 (1991).
"Tensile Bond Force of Glass Ionomer Cements in Direct Bonding of Orthodontic Brackets: An in vitro Comparative Study", F. Rezk–Lega and B. Ogaard, *American Journal of Orthod. Dentofac. Orthop.*, 100, 357–361 (Oct. 1991).
"Orthodontic Bonding Using Glass Ionomer Cement: An in vitro Study", R. Evans and R. Oliver, *European Journal of Orthodontics*, 13, 493–500 (1991).
"In vivo Bonding of Orthodontic Brackets with Glass Ionomer Cement", Voss, A. et al., *The Angle Orthodontist*, 63(2), 149–153 (1993).
"A New Translucent Cement for Dentistry. The Glass Ionomer Cement," A. D. Wilson and B. E. Kent, *Brit. Dent. J.*, 132, 133–135 (1972).
"Glass Ionomer Cement," Larry W. White, *JCO Inc.*, vol. XX, No. 6, 387–391 (1986).
"GC Fuji I. An Improved Glass Ionomer Luting Cement," Brochure distributed by GC International Corp.
"Bond Strength and Durability of Glass Ionomer Cements Used as Bonding Agents in the Placement of Orthodontic Brackets," Klockowski, R., Davis, E., Joynt, R., Wieckowski, G., McDonald, A., *Am. J. Orthod. Dentof. Orthop.*, 96:60–64 (1989).
"Glass Ionomers for Direct Bonding: An In Vitro Assessment," Tavas, M.A., *Br. J. Orthod.*, 17:223–28 (1990).

"Bond Strength of Light–Cured Fluoride–Releasing Base–Liners as Orthodontic Bracket Adhesives," McCourt, J. W., Cooley, R. L., Barnwell, S., *Am. J. Orthod. Dentof. Orthop.*, 100:47–52 (1991).
"Cariostatic Effect and Fluoride Release From a Visible Light–Curing Adhesive for Bonding Orthodontic Brackets," Ogaard, B., Rezk–Lega, F., Ruben, J., and Arends, J., *Am. J. Orthod. Dentofac. Orthop.*, 101:(4) 303–307 (1992).
"Fluoride Concentration in Plaque Adjacent to Orthodontic Brackets Retained with Glass Ionomer Cement," Hallgren, A., Oliveby, A., Twetman, S., *Caries Res.*, 27:51–54 (1993).
"Caries Protection After Orthodontic Band Cementation with Glass Ionomer Cement," Marcushamer, M. Garcia–Godoy, F., Chan D.C.N., *ASDC*, 60 (special issue):300–309 (1993).
"Glass Ionomer Update," Warren Hamula, David W. Hamula, Kelly Brower, *JCO*, vol. XXVII, No. 8, 420–425 (Aug. 1993).
"Comparative SEM Studies of the Enamel Surface Appearance Following the Use of Glass Ionomer Cement and a Diacrylate Resin for Bracket Bonding," E. Ostman–Andersson, A. Marcusson, P. Horstedt, *Swed. Dent. J.*, 17:139–146 (1993).
"Direct Bonding with Glass Ionomer Cement," P. A. Cook, *JCO*, vol. XXIV, No. 8, 509–511 (Aug. 1990).
"Bond Strength of Orthodontic Brackets Using a New Glass Ionomer," V. P. Joseph, A. M. P. Harris, S. R. Grobler, *J. Dent. Res.*, 73, IADR Abstracts, pp. 197, No. 767 (1994).
"A 12–Month Clinical Evaluation of a Glass Polyalkenoate Cement for the Direct Bonding of Orthodontic Brackets," J. P. Fricker, *Am. J. Orthod. Dentofac. Ortho.*, vol. 101, No. 4, 381–384 (Apr. 1992).
"A Preliminary Report on the Effect of Storage in Water on the Properties of Commercial Light–Cured Glass–Ionomer Cements," J. W. Nicholson, H. M. Anstice, J. W. McLean, *Br. Dent. J.*, 173:98–101 (1992).
"Shear Bond Strength of Orthodontic Brackets Bonded with Four Cements," Supak, L. A. et al., IADR Abstract (1994).
"The Effects of Light Cured Glass Ionomer Restorative Materials on Enamel Remineralization Adjacent to Orthodontic Brackets," Althaus, S. et al., IADR Abstract (1994).
"Debond Shear Force of Light Cured Glass Ionomer Adhesives," Kao, E. C. et al., IADR Abstract (1994).

*Primary Examiner*—Nicholas D. Lucchesi
*Attorney, Agent, or Firm*—Synnestvedt & Lechner

[57] ABSTRACT

A method for attaching an orthodontic bracket having a mounting surface to the surface of a tooth comprising: (A) placing, in the presence of the saliva, a cement, which is capable of setting in the presence of saliva, between the surface of the tooth and the mounting surface; and (B) attaching the bracket to the tooth by permitting the cement to bond, in the presence of saliva, to both the surface of the tooth and the mounting surface of the bracket, a preferred class of cement for use in the present invention being a glass ionomer cement, more preferably a light-curable glass ionomer cement.

20 Claims, No Drawings

ATTACHMENT OF ORTHODONTIC BRACKETS

CROSS-REFERENCE TO RELATED APPLICATION

This is a continuation-in-part of U.S. application Ser. No. 08/215,266, filed Mar. 21, 1994, now abandoned.

FIELD OF THE INVENTION

The present invention relates to securing orthodontic appliances to the teeth. More particularly, the present invention relates to improved means for attaching an orthodontic bracket to a tooth, including the use of an adhesive.

Orthodontics is a dental specialty involving the prevention and correction of irregularities in the orientation of the teeth. One way of accomplishing this involves the use of wire-receiving brackets which are mounted on individual teeth and of wire which is attached to the brackets in a manner such that the wire exerts on the teeth a force which causes them to move into the desired orientation in the mouth.

There has been a continuous search in orthodontics for optimal methods of attaching the wire-receiving brackets onto the teeth. In the past, these brackets were often attached to a metal band which was circumposed around a given tooth, thereby securing the bracket on the tooth. However, the presence of the bands on the teeth often resulted in undesirable effects relating to difficulties in cleaning the teeth. Accordingly, there has been a movement in orthodontics towards the use of brackets which do not require the use of a securing band. The mounting of such brackets is accomplished by the use of cements which are optimized for their ability to interact with the surface of a tooth and the bracket. The present invention relates to an improved method for attaching such a bracket to the surface of a tooth utilizing cement.

Reported Developments

Present orthodontic practices generally include attachment of an orthodontic bracket to acid-etched teeth utilizing an adhesive or cement comprising either acrylic or diacrylic resins. An example of such a resin is the adhesive sold by 3M Corporation under the trademark CONCISE. The use of such resins to attach brackets is disclosed, for example, in U.S. Pat. No. 3,895,445 to Silverman and Cohen. This patent discloses an adhesive composition comprising a thermosetting resin in combination with a methyacrylic acid ester for attaching brackets to teeth. Such compositions are referred to hereafter as "composite resins". Although bonding brackets directly to the teeth utilizing such composite resins has found widespread use, there are a number of undesirable effects which result from utilization of such composite resins.

To apply orthodontic brackets utilizing a composite resin, the enamel of the teeth is etched prior to attaching the brackets. This etching irreversibly damages the enamel surface and partial loss of enamel has been reported when removing both metal and ceramic brackets. Furthermore, the methods of clean-up which are effective in removing the composite resin may scratch and possibly crack the enamel surface, resulting in further damage to the teeth. It has also been found that decalcification occurs around the bracket periphery within a few weeks of bracket placement. Finally, it has been observed that some patients exhibit a skin reaction to the bonding resins. Accordingly, there has been a search for alternative methods that would avoid the problems encountered with use of the aforementioned type of composite resins.

Recently, there has been interest in the use of glass ionomer cements to attach orthodontic brackets to teeth. Glass ionomer cements generally comprise a binder and a setting composition. When combined, the binder and setting composition enable the cement to bond to both the surface of a tooth and the bracket. In the most basic glass ionomer cements, the binder is composed of a glass powder and the setting composition is a concentrated solution of a polyacrylic acid. Glass ionomer cements such as Vitrabond, sold by 3M Dental Products Division, include additional components which cure upon exposure to light. It has been reported that there is no need to etch teeth prior to the use of a glass ionomer cement.

To determine whether the various glass ionomer cements provide a sufficiently strong bond to teeth and whether they are superior to prior art composite resins, a number of studies have been done to test the tensile bond strength of various glass ionomer cements. These studies have primarily involved in vitro experiments wherein a bracket is bonded to an extracted tooth and a mechanical device is used to pull the bracket off of the tooth while providing a measurement of the force exerted on the bracket. Most of these studies determined that the prior art composite resin adhesives have greater tensile bond strengths than those possessed by glass ionomer cements. For example, see the publication entitled "Glass Ionomer Cements Used in Bonding Materials for Metal Orthodontic Brackets. An in vitro Study", Oen, J. O. et al., *European Journal of Orthodontics*, 13, 187–191 (1991). This publication discloses the results of work which examined the bond strength of orthodontic brackets bonded to teeth with various glass ionomer cements. Strength measurements were also conducted using composite resins. The results of these studies indicated that the bond strength was considerably lower for glass ionomer cements compared with the strength of bonds formed with composite resins.

In the publication entitled "Tensile Bond Force of Glass Ionomer Cements in Direct Bonding of Orthodontic Brackets: An in vitro Comparative Study", F. Rezk-Lega and B. Ogaard, *American Journal of Orthod. Dentofac. Orthop.*, 100, 357–361 (October 1991), the bond strength of glass ionomer cements was tested in vitro and compared to composite resins. These results also indicated that the composite resin had a higher tensile bond strength than that of each of the glass ionomer cements examined. In the publication entitled "Orthodontic Bonding Using Glass Ionomer Cement: An in vitro Study", R Evans and R. Oliver, *European Journal of Orthodontics*, 13, 493–500 (1991), the tensile bond strength of glass ionomer cements and the effects of moisture contamination of the cement were examined. These studies indicated that the bond strength for each of the composite resins was in excess of the bond strength for any of the tested glass ionomer cements. In the publication "In vivo Bonding of Orthodontic Brackets with Glass Ionomer Cement", Voss, A. et al., *The Angle Orthodontist*, 63(2), 149–153 (1993), the ability of the glass ionomer cements to bond in vivo was examined. This publication demonstrated that it was possible to bond brackets to a patient's teeth using the glass ionomer cements and provided information on the bonding strength of the cement.

In the publication entitled, "Bond Strength and Durability of Glass Ionomer Cements Used as Bonding Agents in the Placement of Orthodontic Brackets," Klockowski, R., Davis, E., Joynt, R., Wieckowski, G., McDonald, A., *Am. J.*

*Orthod. Dentof. Orthop.*, 96:60–64 (1989) it is pointed out that conventional orthodontic bonding agents had higher bonding strengths than glass ionomer cement materials. In the publication entitled "Glass Ionomers for Direct Bonding: An In Vitro Assessment," Tavas, M. A., *Br. J. Orthod.*, 17:223–28 (1990), the authors determined that the glass ionomer cements examined obtained maximal strength at 24 hours.

A number of additional studies have been undertaken to evaluate the bond strength of glass ionomer cements, including light-curable glass ionomer cements, when used as orthodontic bracket adhesives. In the publication "Bond Strength of Light-Cured Fluoride-Releasing Base-Liners as Orthodontic Bracket Adhesives," McCourt, J. W., Cooley, R. L., Barnwell, S., *Am. J. Orthod. Dentof. Orthop.*, 100:47–52 (1991), the authors determined that the tested light-curable glass ionomer cement was not acceptable as an orthodontic bracket bonding agent due to insufficient bond strength.

Many of the above-cited studies suggested that there is room for improvement in the formulations of glass ionomer cements and in almost all of these studies, conventional orthodontic bonding agents were found to have higher bonding strength than the strength provided by glass ionomer cements.

It has been recognized that the glass ionomer cements are advantageous in their ability to release fluoride over prolonged periods of time. This offers the possibility of reducing the formation of caries in association with fixed orthodontic appliances. Accordingly, a number of studies have been directed to quantification of the fluoride release and effect on caries development of glass ionomer cements when used to bond brackets to teeth. Examples of such studies include Ogaard, B., Rezk-Lega, F., Ruben, J., and Arends, J., "Cariostatic Effect and Fluoride Release From a Visible Light-Curing Adhesive for Bonding Orthodontic Brackets," *Am. J. Orthod. Dentofac. Orthop.*, 101:(4) 303–307 (1992); Hallgren, A., Oliveby, A., Twetman, S., "Fluoride Concentration in Plaque Adjacent to Orthodontic Brackets Retained with Glass Ionomer Cement," *Caries Res.*, 27:51–54 (1993); and Marcushamer, M. Garcia-Godoy, F., Chan D. C. N., "Caries Protection After Orthodontic Band Cementation with Glass Ionomer Cement," *ASDC*, 60 (special issue):300–309 (1993).

These publications suggest that although glass ionomer cements possess a variety of desirable properties, they do not offer the bond strength provided by the composite resins. Furthermore, these publications emphasize the need to dry the area where the glass ionomer cement is to be applied.

The present invention relates to a more efficient way of using a cement, including heretofore known cements, to attach a bracket to the surface of a tooth.

SUMMARY OF THE INVENTION

In accordance with the present invention, there is provided a method for attaching an orthodontic bracket having a mounting surface to the surface of a tooth comprising: (A) placing, in the presence of saliva, a cement capable of setting in the presence of saliva between the surface of the tooth and the mounting surface; and (B) attaching the bracket to the tooth by permitting the cement to bond, in the presence of saliva, to both the surface of the tooth and the mounting surface of the bracket.

The present invention is based in part on the discovery that a cement capable of setting in the presence of saliva can be used effectively to attach an orthodontic bracket to a tooth in the presence of saliva.

A preferred class of cements for use in the present invention is a glass ionomer cement, most preferably a light-curable glass ionomer cement.

The use of the present invention is particularly advantageous in that it allows an orthodontist to apply brackets to teeth which are located in areas that are very difficult to isolate and keep dry during attachment of the bracket. Prevention of the intrusion of saliva into the site where a bracket is being attached to a tooth is especially difficult in the rear of the mouth where an orthodontist will often apply tubes and brackets to molars which serve as "anchor teeth" for the wire. The presence of the tubes and brackets makes it difficult for the orthodontist to keep this portion of the mouth dry. The present invention allows the orthodontist to apply these tubes and brackets without having to be concerned with the tedious task of trying to keep this portion of the mouth dry.

The ability of a glass ionomer cement to form a secure bond between a tooth and an orthodontic bracket in the presence of saliva was unexpected given prior art teachings that glass ionomer cements lacked sufficient bond strength to retain brackets in place and were particularly vulnerable to the effects of saliva intrusion, especially in view of the constant exposure of the cement to saliva when used to retain a bracket. It is expected that the present invention will be especially useful when mounting orthodontic brackets in the rear of the mouth where the intrusion of saliva and its consequent effects on the strength of the mounted bracket is substantial.

Another aspect of the present invention is that it is not necessary to etch the tooth prior to the application to the tooth of the cement according to the present invention. By way of background, it is noted that etching of teeth involves the use of acids, such as phosphoric acid, which react with the enamel of the tooth and increase the surface area of a tooth by producing microscopic pits. In addition, it is believed that etching results in exposure of the enamel's organic framework which can serve as a network to which various adhesives, such as an acrylic resin, can adhere. Furthermore, it is believed that the removal of the enamel surface exposes a fresh reactive surface more favorable for a variety of bonding reactions.

Etching is to be distinguished from the cleaning of a tooth in which an abrasive material is used to remove from the exposed surface of the tooth foreign materials which are broadly classified as stain and tartar. Stains may result from smoking, tobacco chewing, or excessive drinking of tea, as well as a variety of other causes. There are several different types of tartar, the two most common types being serumal tartar, originating from blood, and salivary tartar, originating from the saliva.

Although advantages are realized by cleaning the tooth in the practice of the present invention, it is not necessary in the practice of the present invention to etch the tooth; indeed, it is preferable to avoid etching the tooth.

Thus, using the method of the present invention, an orthodontist can attach an orthodontic bracket in the presence of saliva, eliminating the requirements of prior art methods that a tooth be isolated from saliva, dried, and etched prior to bracket attachment. The phrase "in the presence of saliva" means that saliva is present at the site where the bracket is being attached to a tooth by a cement as described herein, that is, a cement which is capable of setting in the presence of saliva.

DETAILED DESCRIPTION OF THE INVENTION

Any suitable cement that is capable of adhering the surface of the orthodontic bracket to the surface of a tooth and which is capable of setting in the presence of saliva can be used in the practice of the present invention. For use with a human patient, the components of the cement should be stable before and after mixing. In addition, cements used with human patients should be, following mixing, thick enough to hold a bracket in place and they preferably should partially set to close to their maximum strength within about sixty seconds. It is desirable also that excess cement be easily removable without disturbing the position of the bracket on the patient's tooth. In addition, the cements used with human patients should be of a color which is substantially similar to the color of the teeth.

Examples of classes of cements that are useful in the practice of the present invention include glass ionomer cements and cements based on barnacle cements. Glass ionomer cements, more preferably light-curable glass ionomer cements, are preferred for use in the practice of this invention.

Glass ionomer cements are comprised of a binder and a setting composition, referred to hereafter as a "setting reactant". The binder component of the glass ionomer cement is combined with the setting reactant. When so combined, the binder and setting reactant solidify and are able to bond to both the surface of the tooth and a metal, ceramic or plastic orthodontic bracket.

In preferred embodiments of conventional glass ionomer cements, the binder is a fluoroaluminosilicate glass, especially a fluoroaluminosilicate glass prepared by blending together about 37 to about 45% by weight of silicic anhydride, about 25 to about 35% by weight of aluminum oxide, about 5 to about 13% by weight of calcium oxide, about 10 to about 15% by weight of soda fluoride and about 3 to about 7% by weight of calcium phosphate and firing the resultant blend at about 1,300° C. A particularly preferred binder is a powder formulated by heat treatment at about 1300° C. of about 40% by weight of silica sand, about 26% by weight of alumina, about 12% by weight soda fluoride, about 15% by weight of lime carbonate and about 7% by weight of lime phosphate.

In preferred embodiments of conventional glass ionomer cements, the setting reactant of the cement includes four components: a cross-linking polymer, a setting enhancer, a fluorocomplex salt and water.

The cross-linking polymer is preferably a copolymer of acrylic acid and maleic acid. In a most preferred embodiment, the copolymer of acrylic acid and maleic acid has a mean molecular weight of no more than about 30,000, particularly about 5,000 to about 20,000. The mean molecular weight is calculated using the formula provided in U.S. Pat. No. 4,342,677 which discloses a fluorocomplex salt-containing liquid for setting dental cements. It is particularly preferred to use a copolymer of acrylic acid and maleic acid in which the acrylic acid comprises about 60 wt % or more of the copolymer. Particularly preferred embodiments utilize a copolymer of about 80 to about 90 wt% acrylic acid and about 10 to about 20 wt % of maleic acid and the copolymer comprises about 45 to about 55% by weight of the total weight of the setting reactant.

The setting enhancer is preferably tartaric acid, typically used in a proportion of about 10 to about 25 wt %, preferably about 10 to about 15 wt %, based on the total weight of the setting reactant.

The fluorocomplex salts may be any of the fluorocomplex salts disclosed in U.S. Pat. No. 4,342,677. Particularly preferred fluorocomplex salts are potassium tetrafluoroberyllate, sodium hexafluorozirconate, potassium hexafluorozirconate and mixtures thereof. In most preferred embodiments, the setting reactant comprises about 45 to about 55 wt % of a copolymer of acrylic acid and maleic acid containing tartaric acid and one or more fluorocomplex salts in an amount of about 0.1 to about 5% on the basis of the total weight.

Water typically comprises about 38 to about 50 wt. %, preferably about 38 to about 44 wt. % based on the total weight of the setting reactant.

It is anticipated that glass ionomer cements which contain additional ingredients which permit light activation of polymer crosslinking and curing of the cement may be utilized in the practice of the present invention. Indeed, the most preferred embodiment of glass ionomer cements for use in the practice of the present invention are such cements. In light-activated glass ionomer cements, the light source used to activate the polymer may be ultra-violet (UV) or white light. An example of a light-activated glass ionomer cement is Vitrabond which is manufactured by 3M Dental Products Division.

Light-activated glass ionomer cements are similar to the conventional glass ionomer cements discussed hereinabove in that they include a binder and setting reactant. They include additionally other ingredients which are cured by light-activation. As the term is used herein, "light-curable glass ionomer cement" refers to a glass ionomer cement which includes a binder, a setting reactant, and also a photoactivated curable material which undergoes polymerization upon exposure to light. The set product of such a cement is referred to herein as a "light-cured glass ionomer cement".

A preferred light-curable glass ionomer cement for use in the practice of the present invention is described in U.S. Pat. No. 5,063,257, the disclosure of which is incorporated herein by reference. This patent discloses the following composition for use in other types of dental applications, for example, use in the cementing of inlays and crowns, filling of caries cavities and the lining and preventive sealing of pits and fissures:

(A) a polymer of an α-β unsaturated carboxylic acid having a weight average molecular weight of about 5,000 to about 40,000;

(B) a fluoroaluminosilicate glass powder having a mean particle size of about 0.02 to about 10 μm and a specific gravity of about 2.4 to about 4 and capable of reacting with the polymer of (A) above;

(C) a polymerizable unsaturated organic compound containing at least one $CH_2=C(R1)-COO-$ group, wherein $R1=H$ or $CH_3$;

(D) a polymerization catalyst;

(E) water;

(F) a surface active agent; and (G) a reducing agent.

Comparing a light-curable glass ionomer cement of the above type to a conventional glass ionomer cement, the latter comprises ingredients (A)—a setting reactant—and (B)—a binder—and (E)—water—, whereas the light-curable glass ionomer cement includes additional ingredients (C), (D), (F) and (G) which play a role in the light-catalyzed setting reaction of the cement. For example, ingredient (C)—the polymerizable unsaturated organic compound— provides for a quick setting reaction of the cement when exposed to visible light irradiation in the presence of ingredient (D)—a polymerization catalyst—preferably a photopolymerization catalyst. Ingredient (G)—a reducing agent—accelerates the reaction and ingredient (F)—a surface active agent—functions to form an emulsion comprising the polymerizable unsaturated organic compound uniformly distributed in an aqueous phase.

An example of a visible light-curing device for use with the above type composition is a device which produces light having a wavelength of about 470 nm which triggers activation of the polymerization catalyst.

The presence of both the binder and setting reactant and the photoactivated curable material results in dual setting reactions in which the binder and setting reactant undergo an acid-base reaction upon mixing. The photoactivated curable material reacts upon exposure to light. This reaction results from free radical polymerization of the polymerizable unsaturated organic compound resulting in the formation of a polymer matrix which quickly hardens the cement. The acid base reaction between the binder and setting reactant continues after the cement has been cured by light irradiation. It is believed that the photoactivated curable material and the polyacrylic acid metallic salt formed by the binder and setting reactant form a homogeneous matrix surrounding the glass particles of the cement.

The setting reactant comprises a polymer of an α-β unsaturated carboxylic acid, preferably a copolymer of acrylic and maleic acid having an average molecular weight of about 5,000 to about 40,000 in the form of a liquid. The polymer of the α-β-unsaturated carboxylic acid is used in an amount of about 5 to about 100 parts by weight in the composition of the present invention.

In preferred embodiments, the binder is an fluoroaluminosilicate glass powder. It is particularly preferred that the glass contains as its main components $Al^{3+}$, $Si^{4+}$, $F^-$, $O^{2-}$, $Ca^{2+}$ and/or $Sr^{2+}$. It is preferred also that out of the total weight of the glass, aluminum counts for about 10 to about 21% by weight, silicon about 9 to about 24% by weight, fluorine about 1 to about 20% by weight, and strontium and calcium about 10 to about 34% by weight. The glass powder used in the present invention preferably has a mean particle size of about 0.02 to about 10 micrometers and a specific gravity of about 2.4 to about 4. It should be capable of reacting with the polymer of an α,β unsaturated carboxylic acid present in the setting reactant. The glass powder is used in an amount of about 5 to about 100 parts by weight in the compositions of the present invention.

The photoactivated curable material comprises a polymerizable unsaturated organic compound having at least one $CH_2=C(R_1)$—COO— group, wherein $R_1$=H or $CH_3$. More specifically, polymerizable unsaturated organic compounds having an acryloyl or methacryloyl group which is unreactive with the fluoroaluminosilicate glass powder are preferred. In preferred embodiments, an ester of acrylic or methacrylic acid, such as methyl methacrylate and similar compounds are used. In particularly preferred embodiments, HEMA (2-hydroxyethylmethacrylate) is used in an amount ranging from about 5 to about 100 parts by weight in the composition of the present invention and is combined with the setting reactant.

The binder can additionally include a polymerization catalyst, preferably a photopolymerization catalyst or initiator Catalysts such as benzyl, p, p', dimethoxybenzyl, p, p', dichlorobenzyl and camphorquinone may be used In preferred embodiments, camphorquinone is utilized. The polymerization catalysts are preferably used in an amount ranging from about 0.01 to about 5 parts by weight in the composition of the present invention.

Water serves as a solvent in aqueous solutions containing components of the setting reactant. In preferred embodiments, distilled water is utilized. Preferred embodiments of the present invention include about 2 to about 50 parts by weight of water in the composition of the present invention.

In preferred embodiments, the setting reactant and photoactivated curable material are combined and maintained in liquid form until the cement is prepared for use. However, certain components of the setting reactant and photoactivated curable material may be immiscible in water. As an example, it has been observed that various preferred polymerizable unsaturated organic compounds are immiscible in water. Adding a surface active agent to an aqueous solution which contains the other components of the setting reactant and the photoactivated curable material appears to result in the formation of an emulsion. This aids in uniformly distributing the polymerizable unsaturated organic compound in the aqueous solution.

It is anticipated that any surface active agent which is capable of forming an emulsion may be used in the present invention. Examples of surface active agents include sorbitin fatty acid esters and glycerin fatty acid esters. The surface active agent is present in amounts ranging from about 0.01 to about 10 parts by weight in the composition of the present invention and is preferably included in the setting reactant.

The polymerization catalyst may be used in combination with a reducing agent to make the curing proceed more rapidly. Examples of reducing agents which may be used in the practice of the present invention include dimethylaminoethylmethacrylate, n-butylamine, triethylamine, and other reducing agents, such as those disclosed in U.S. Pat. No. 5,063,257. The reducing agent is used in amounts ranging from about 0.01 to about 5 parts by weight (pbw) in the composition of the present invention and is preferably included in the setting reactant.

It is generally preferred that the light-curable glass ionomer cement be prepared by combining aforementioned ingredients (A) through (G) and exposing the mixture to light when it is ready to be used. In a normal procedure, the area to which the bracket is to be applied will be cleaned with pumice and water and rinsed, but not desiccated. The binder (B) is usually present in the form of a powder. Ingredients (A) and (C) through (F) are typically in the form of a liquid. The powdered binder and liquid setting reactant are combined and mixed to form a homogeneous paste. The paste-like consistency of the cement facilitates its application to the bracket.

Mixing and application of the cement can be effected at room temperature, that is, from about 21° C. to about 25° C. Once the binder and setting reactant are combined, the acid-base reaction between the reactants begins. The cement may be manipulated until the acid-base reaction renders the paste too viscous for further manipulation and hardening of the cement is evident, for example, within about three minutes after mixing. Lower temperatures have been found to increase the time available to manipulate the cement, sometimes referred to as "working time" and higher temperatures will decrease the working time.

During the period of working time, the cement is applied conveniently to the back or mounting surface of the bracket. Any suitable orthodontic bracket for a given treatment is acceptable. For example, brackets made of metal, ceramic and plastic may be used. The bracket is then placed against the surface of the given tooth and excess cement is removed.

Following application of the bracket to the tooth, a light-curing device is directed at each of the mounted brackets to trigger activation of the polymerization catalyst. In preferred embodiments, the light-curing device produces light in the visible spectrum. The cement is exposed to the light-curing device for a sufficient period of time to ensure the initiation of polymerization of the polymerizable unsaturated organic compound.

Based on the light-catalyzed reaction, the cement composition of the present invention quickly reaches the adhesive strength required to maintain a bracket in place.

As mentioned hereinabove, the photocatalyzed reaction proceeds at a faster rate than the acid-base reaction of the reactants. The acid base reaction continues after the bracket has been mounted and the cement has been cured by light irradiation. In preferred embodiments, maximal strength is reached within about 5 minutes to about 10 minutes after the bracket has been applied.

Following attachment of the brackets to the teeth, typical treatment of a patient involves engaging a stainless steel wire in the wire receiving-portion of the brackets and placing the ends of the wire in anchor tubes which are usually mounted on the molars. The wire is positioned on the brackets to exert a force on the teeth such that the teeth are moved into the desired position in the mouth.

There are a number of significant forces exerted against wire-receiving orthodontic brackets in a patient's mouth. One of these forces consists of the stress exerted against an orthodontic bracket when a patient chews food. Additional forces result from stress due to the interaction between the force exerted by the wire and the resistance of the teeth to this force. In particular, a bracket mounted on an individual tooth encounters a shear stress involving forces that pull the bonded bracket substantially upwardly and parallel to the tooth's surface. The bracket will additionally encounter forces directed substantially perpendicular to and away from the surface of the tooth. It is believed that such forces, which are tensile in nature, create the greatest stress in the course of treatment and are often responsible for detachment of brackets from a tooth's surface.

Although a variety of prior art cements, particularly the aforementioned acrylic resins of the prior art, are capable of forming bonds having the desired strength, their use requires etching of the teeth and additionally requires longer periods of time to actually affix the orthodontic brackets to the patient's teeth. Prior art glass ionomer cements have been used in applications where the forces encountered by the cement are different from the forces encountered in orthodontic therapies. In particular, the forces encountered by glass ionomer cements in the cementing of inlays, crowns, filling of cavities and lining and sealing of pits and fissures include compressive, diametral tensile and flexural forces.

In contrast to prior art cements, the cement of the present invention permits the orthodontist to mount the wire in the brackets very soon after attachment of the bracket. Furthermore, the bond between the tooth and the bracket retains its strength over the relatively long periods of time that are needed for effective treatment. As an example, periods of orthodontic treatment typically range from about one to about two years for treatment of an overbite.

To remain in place and counter the forces encountered by the mounted bracket during treatment, the cement of the present invention possesses a minimal adhesive strength of about 6–8 megapascals. As discussed hereinabove, the cement composition may be applied in the presence of saliva and it forms a bond of significant and satisfactory strength despite being exposed to a saliva environment immediately upon application.

There are a number of methods available for testing the adhesive bond strength of orthodontic cements. Examples of such methods are presented in McCourt, James W. et al., *Am. J. Orthod. Dentofac. Orthop.*, Vol. 100, No. 1, pp. 47–52 (July 1991) and Klockowski, Richard et al., *Am. J. Orthod. Dentofac. Orthop.*, Vol. 96, No. 1, pp. 60–64 (July 1989).

The method described in the McCourt et al. publication involves application of an orthodontic bracket to a tooth in vitro and testing the bracketed tooth on an Instron universal testing machine (Instron Engineering Co., Canton, Mass.). A shearing blade is placed so as to contact the bracket at its base and the force at which the bracket is sheared from the tooth is calculated in megapascals using the surface area of the bracket, as determined using a measuring microscope.

The following examples are illustrative of the practice of the present invention.

The first example is illustrative of the use of a glass ionomer cement in the practice of the present invention.

EXAMPLE 1

The teeth of a male patient in need of orthodontic treatment were cleaned with polishing brushes and pumice in preparation for the attachment of orthodontic brackets. To attach the brackets, a glass ionomer cement, sold under the trade name GC Fuji-1 and manufactured by GC Corporation, was used. It is believed that this cement is the type of cement described in U.S. Pat. No. 4,342,677 to Muramatsu et al. This patent discloses a setting reactant comprising a copolymer of acrylic acid and maleic acid, tartaric acid, and one or more fluorocomplex salts. To form the glass ionomer cement, this setting reactant is combined with a binder comprising a fluoroaluminosilicate glass powder, for example, the dental cement powder manufactured by G.C. Dental Industrial Corp. and sold under the trade name NEW LUSILEX.

The Fuji-1 glass ionomer cement is provided as a kit with a package of the binder in the form of a powder and the setting reactant in liquid form. To prepare the cement, 1.8 grams of the binder powder included in the package was divided into two equal portions and 1 gram of the liquid setting reactant was mixed for ten seconds with the powder using a plastic spatula. Following this initial mixing, the remaining portion of the powder was added to the mixture and mixed thoroughly for an additional ten seconds.

When mixed together, the powder and setting reactant formed a paste. This paste was sufficiently viscous to be manipulated and remain in place when applied to a surface. Using a spatula, the paste was applied to the back of an orthodontic bracket sold under the tradename Edgewise and manufactured by G.A.C. International. The orthodontic bracket was gently pressed against the surface of a given tooth so that the paste on the mounting surface of the bracket came into contact with the surface of the tooth.

These procedures were performed in the presence of saliva and no effort was made to prevent the intrusion of saliva during the application of the brackets. In particular, when applying the brackets to the rear molars, the brackets were mounted onto the teeth despite the presence of saliva.

After initial placement of the bracket, the excess cement was removed using a scaler. The bracket was allowed to rest in place for approximately three minutes while the cement hardened.

Following a period of five minutes, stainless steel wire of 0.016 inch diameter was formed into an ideal arch and engaged in the orthodontic brackets so as to effect the desired tooth movement. The wire was engaged in the wire-receiving portion of the brackets and the ends of the wire were inserted into anchoring tubes mounted on the teeth in the rear of the mouth. It is expected that during the period of treatment, if it becomes necessary to change the moving forces applied to the teeth, the wire may be removed and reapplied as necessary. The orthodontic wire employed was manufactured by G.A.C. International Co.

To remove the brackets, a bracket-removal plier was used. The pliers were positioned such that one beak of the plier gripped the occlusal side of the bracket and the other beak of the plier gripped the gingival side of the bracket. A force was then applied along the long axis of the tooth so as to remove the bracket from the tooth. Following removal of the bracket, the pliers were used to remove any remaining cement residue by planing the surface of the tooth with the edges of the beak of the pliers. Finally, a polishing stone was used to remove any final remnants of the glass ionomer cement left on the tooth.

Follow-up inspections of orthodontic brackets mounted in the aforementioned manner have indicated that the glass ionomer cement provides for secure attachment of the brackets and is resistant to the forces generated during mastication and the forces generated by the wire itself.

EXAMPLE 2

Use of Light-Curable Glass Ionomer Cement

The teeth of a male patient in need of orthodontic treatment were cleaned with polishing brushes and pumice in preparation for the attachment of orthodontic brackets. Following cleaning, the teeth were rinsed well to remove residual pumice. To attach the brackets, a light-curable glass ionomer cement, sold under the trademark FUJI-II LC and manufactured by GC Corporation, was used. It is believed that this cement is the type of cement described in aforementioned U.S. Pat. No. 5,063,257 to Akahane et al. This patent discloses a cement comprising a polymer of an α-β unsaturated carboxylic acid, a fluoroaluminosilicate glass binder, a polymerizable unsaturated organic compound, a polymerization catalyst, water, a surface active agent and a reducing agent.

The FUJI-II LC glass ionomer light-curable cement is provided as a kit with a package of the fluoroaluminosilicate glass binder and polymerization catalyst in the form of a powder and the other components in liquid form. To prepare the cement, approximately three grams of the powder included in the package were divided into two equal portions and one gram of the liquid was mixed with 1.5 grams of the powder for ten seconds using a plastic spatula. Following this initial mixing, the remaining portion of the powder was added to the mixture and mixed thoroughly for an additional ten to fifteen seconds. Total mixing time did not exceed 20–25 seconds.

When mixed together, the powder and liquid formed a paste. The paste was sufficiently viscous to be manipulated and remain in place when applied to a surface. Using a spatula, the paste was applied to the back of an orthodontic bracket sold under the tradename EDGEWISE and manufactured by GAC International. The orthodontic bracket was gently pressed against the surface of a given tooth so that the paste on the mounting surface of the bracket came into contact with the surface of the tooth. Excessive adhesive was expelled from along the margins of the mounting surface of the bracket.

The excess material was carefully removed without disturbing the position of the orthodontic bracket. Once the bracket was located in the desired position on the tooth, a visible light curing device (470 nm wavelength) was directed at each mounted bracket for a period of about 40 seconds. This allowed the cement to quickly reach a high level of adhesive strength.

These procedures were performed in the presence of saliva and no effort was made to prevent the intrusion of saliva during application of the brackets. In particular, when applying the brackets to rear molars, the brackets were mounted on the teeth despite the presence of saliva.

After about five minutes, stainless steel wire of 0.016 inch diameter was formed into an ideal arch and engaged in the orthodontic brackets so as to effect the desired tooth movement. The wire was engaged in the wire-receiving portion of the brackets and the ends of the wire were inserted into anchoring tubes mounted on the teeth in the rear of the mouth. It is expected that during the period of treatment, the wire may be removed and reapplied as necessary if it becomes necessary to change the moving forces applied to the teeth. The orthodontic wire employed was manufactured by G.A.C. International Co.

Follow-up inspections of the orthodontic brackets applied using the aforementioned light-curable glass ionomer cement have indicated that the cement provides for secure attachment of the brackets almost-immediately and is resistant to the forces generated during mastication and the forces generated by the wire itself during the course of orthodontic treatment.

From the above description, it should be appreciated that the present invention has the advantage of greatly simplifying the steps involved in the preparation and mounting of orthodontic brackets and dramatically reduces the amount of time needed for an orthodontist to apply a bracket and orthodontic wires.

We claim:

1. A method for attaching an orthodontic bracket having a mounting surface to the surface of a tooth comprising:

placing, in the presence of saliva, a cement capable of setting in the presence of saliva between the surface of said tooth and said mounting surface; and attaching said bracket to said tooth by permitting said cement to bond, in the presence of saliva, to both the surface of said tooth and said mounting surface.

2. A method for attaching an orthodontic bracket having a mounting surface to the surface of a tooth in a human patient comprising:

placing a glass ionomer cement on the surface of said mounting surface; and attaching said bracket to said tooth in the presence of saliva by permitting said glass ionomer cement to bond, in the presence of saliva, to both the surface of said tooth and said mounting surface.

3. The method of claim 2 wherein said glass ionomer cement comprises a binder and a setting reactant.

4. The method of claim 2 wherein said setting reactant comprises a cross-linking polymer.

5. The method of claim 2 wherein said cross-linking polymer comprises a copolymer of acrylic acid and maleic acid.

6. The method of claim 5 wherein said copolymer of acrylic acid and maleic acid has a mean molecular weight of no more than about 30,000.

7. The method of claim 6 wherein said acrylic acid in said copolymer comprises about 60 wt % of the copolymer.

8. The method of claim 7 wherein said copolymer comprises about 80 to about 90 wt % acrylic acid and about 10 to about 20 wt % maleic acid.

9. The method of claim 2 wherein said cement includes also a setting enhancer.

10. The method of claim 9 wherein said setting enhancer consists essentially of tartaric acid.

11. The method of claim 10 wherein said tartaric acid comprises about 10 to about 25 wt % of the total weight of the setting reactant.

12. The method of claim 2 wherein said glass ionomer cement further comprises a fluorocomplex salt.

13. The method of claim 12 wherein said fluorocomplex salt is selected from the group consisting of potassium tetrafluoroberyllate, sodium hexafluorozirconate, potassium hexafluorozirconate, zinc hexafluorosilicate, magnesium hexafluorosilicate, sodium hexafluorotitanate, potassium hexafluorotitanate and ammonium hexafluorotitanate.

14. The method of claim 2 wherein said tooth is not etched.

15. The method according to claim 2 wherein said glass ionomer cement is a light-curable glass ionomer cement that bonds said bracket to a human tooth, and including subjecting said cement to a light source which effects curing of said cement.

16. The method of claim 15 wherein said light-curable glass ionomer cement comprises a polymer of $\alpha$-$\beta$ unsaturated carboxylic acid, a fluoroaluminosilicate glass powder, a polymerizable unsaturated organic compound $CH_2=C(R_1)-COO-$ Group wherein $R_1=H$ or $CH_3$, water and a polymerizable catalyst.

17. The method of claim 16 wherein said light-curable glass ionomer cement further comprises a surface active agent and a reducing agent.

18. The method of claim 16 wherein said polymer of $\alpha$-$\beta$ unsaturated carboxylic acid has an average molecular weight of about 5,000 to about 40,000.

19. The method of claim 16 wherein said fluoroaluminosilicate glass powder comprises a fluoroaluminosilicate glass powder having a mean particle size of about 0.02 to about 10 µm and a specific gravity of about 2.4 to about 4.

20. The method according to claim 16 wherein said polymerizable unsaturated organic compound is 2-hydroxyethylmethacrylate.

* * * * *

UNITED STATES PATENT AND TRADEMARK OFFICE
CERTIFICATE OF CORRECTION

PATENT NO. :   5,593,303
DATED      :   January 14, 1997
INVENTOR(S):   Morton Cohen and Elliott Silverman It is certified that error appears in the above-identified patent and that said Letters Patent is hereby corrected as shown below:

Column 14, line 22, after Claim 20, insert Claims 21 through 25, as follows.

21. The method of Claim 1 wherein said cement possesses a minimum adhesive strength of at least about 6-8 megapascals.

22. The method of Claim 2 wherein said glass ionomer cement possesses a minimum adhesive strength of at least about 6-8 megapascals.

23. The method of Claim 14 wherein said glass ionomer cement possesses a minimum adhesive strength of at least about 6-8 megapascals.

UNITED STATES PATENT AND TRADEMARK OFFICE
CERTIFICATE OF CORRECTION

PATENT NO. : 5,593,303

DATED : January 14, 1997

INVENTOR(S) : Morton Cohen and Elliott Silverman

It is certified that error appears in the above-identified patent and that said Letters Patent is hereby corrected as shown below:

24. The method of Claim 15 wherein said glass ionomer cement possesses a minimum adhesive strength of at least about 6-8 megapascals.

25. The method of Claim 15 wherein said tooth is not etched.

Signed and Sealed this

Fifteenth Day of April, 1997

*Attest:*

BRUCE LEHMAN

*Attesting Officer*     *Commissioner of Patents and Trademarks*